United States Patent
Betcher (10) Patent No.: US 6,482,168 B1
(45) Date of Patent: Nov. 19, 2002

(54) UPPER EXTREMITY HAND ORTHOSIS AND METHOD OF USE

(76) Inventor: Russell A. Betcher, 1125 Weisgarber Rd., Knoxville, TN (US) 37909

( * ) Notice: Subject to any disclaimer, the term of this patent is extended or adjusted under 35 U.S.C. 154(b) by 0 days.

(21) Appl. No.: 09/910,193

(22) Filed: Jul. 20, 2001

(51) Int. Cl.$^7$ .............................. A61F 5/00; A61F 5/37
(52) U.S. Cl. ...................... 602/21; 128/878; 128/879
(58) Field of Search .................. 602/21, 22; 482/49, 482/47, 44; 128/878, 879, 880

(56) References Cited

U.S. PATENT DOCUMENTS

| | | | | |
|---|---|---|---|---|
| 3,606,316 A | * | 9/1971 | Krewer | 482/47 |
| 3,762,401 A | | 10/1973 | Tupper | |
| 4,441,487 A | * | 4/1984 | Daugherty et al. | 132/73 |
| 4,628,911 A | | 12/1986 | Bornstein | |
| 5,076,569 A | * | 12/1991 | Gootter | 482/49 |
| 5,312,197 A | * | 5/1994 | Abramson | 15/105 |
| 5,327,918 A | * | 7/1994 | Stewart et al. | 128/879 |
| 5,340,067 A | * | 8/1994 | Martin et al. | 248/118.5 |
| 5,396,222 A | * | 3/1995 | Markus et al. | 340/679 |
| 5,403,008 A | * | 4/1995 | Mainiero | 473/201 |
| 5,485,856 A | * | 1/1996 | Buckland | 128/879 |
| 5,533,949 A | * | 7/1996 | Hwang | 446/397 |
| 5,765,228 A | | 6/1998 | Bieling | |
| 5,766,142 A | | 6/1998 | Hess | |
| 5,820,522 A | * | 10/1998 | Smallwood et al. | 482/47 |
| 5,855,209 A | | 1/1999 | Hernandez et al. | |
| 5,921,945 A | | 7/1999 | Gray | |

* cited by examiner

*Primary Examiner*—Michael A. Brown
*Assistant Examiner*—Fenn C Mathew
(74) *Attorney, Agent, or Firm*—Pitts & Brittian, PC

(57) ABSTRACT

A hand orthosis includes a body having an oblate spheroid shape and an ellipsoidal surface. The hand orthosis is positioned against the palm of a patient's hand for separating a patient's fingers and thumb from contacting each other. A plurality of finger grooves are indented in substantially parallel and spaced apart configuration across the ellipsoidal surface. A first and a second angled groove is positioned on opposed sides of the plurality of finger grooves for placement of either thumb therein. The hand orthosis is fastened within the patient's palm by means for fastening to maintain separation of the fingers and thumb from each other for extended periods of time. A method of utilizing the hand orthosis during a medical treatment procedure is also disclosed.

20 Claims, 7 Drawing Sheets

UPPER EXTREMITY HAND ORTHOSIS AND METHOD OF USE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of Invention

The present invention relates to a hand orthosis placed in the palm of the hand during medical procedures. More specifically, this invention relates to a hand orthosis placed in the palm of the hand for support and separation of the fingers and thumb, and a method of utilizing the hand orthosis during a medical procedure.

2. Description of the Related Art

Prior devices have provided rigid restraining devices that enclose the fingers of a hand for separation of the fingers by notches or loops into which each finger is inserted. One restraining device is generally rigid and is shaped in a flat configuration for maintaining the palm and fingers in the same plane. Another restraining device is generally rigid and is shaped in a curved configuration for extending the fingers at an angle upwards or downwards from the plane in which the palm is maintained. The prior devices are worn as gloves or as a partially enclosing, generally rigid, orthotic splint designed to immobilize the fingers and palm of the hand during a surgical procedure such as a shoulder arthroscopy. The prior devices typically do not allow the wearer's fingers and thumb to repetitively grip and relax without touching each other, while maintaining the fingers and thumb in a natural curvature during a surgical procedure performed on the patient.

BRIEF SUMMARY OF THE INVENTION

In the present invention, there is provided a hand orthosis for support of a patient's fingers and thumb in a spaced apart configuration, and for separation of the fingers and thumb from contact with each other or with the palm of the hand for an extended period of time. The hand orthosis includes a body having an ellipsoidal surface and an oblate spheroid body having a major axis and a minor axis. A plurality of grooves are indented in the ellipsoidal surface in spaced apart configuration, and are positioned in substantially parallel relation to each other along the ellipsoidal surface for placement of each one of the patient's fingers within each respective groove. First and second thumb grooves are indented on opposed sides of the plurality of grooves. Each first and second thumb groove is angularly spaced apart from the plurality of grooves along the ellipsoidal surface for placement of a thumb therein. A means for fastening is connectable to the ellipsoidal surface for fastening the oblate spheroid body against the palm of the hand. The plurality of grooves maintain the fingers and thumb of the hand in a spaced apart and curved configuration without allowing the fingers and thumb to contact each other during extended periods of time. The present invention includes a method for utilizing the hand orthosis having an oblate spheroid shape and a plurality of grooves for placement of a patient's fingers and thumb therein during a medical treatment procedure performed on the patient.

DETAILED DESCRIPTION OF THE INVENTION

Figure 1:
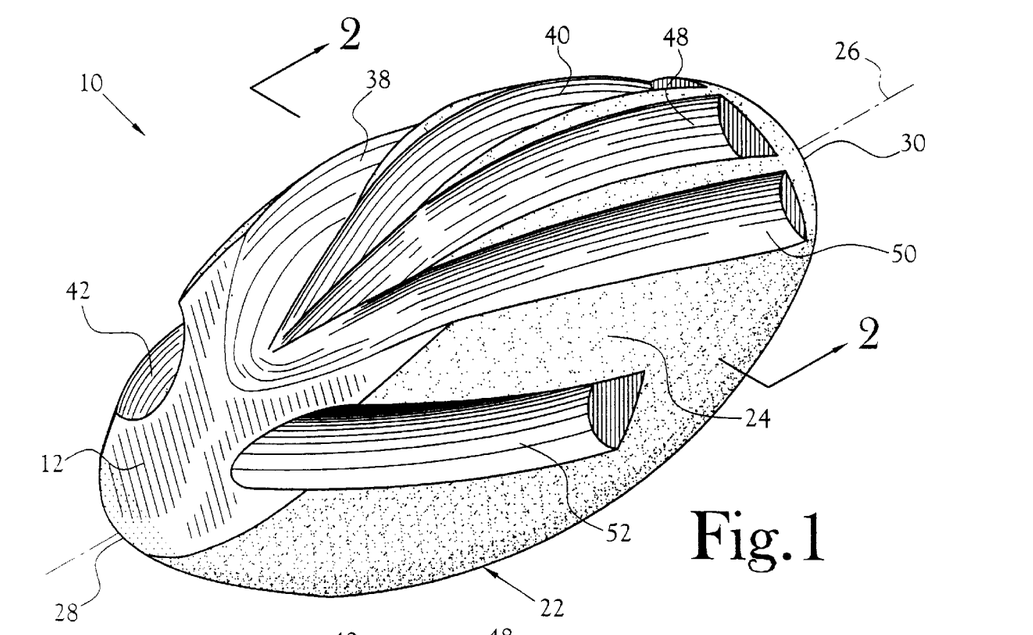
FIG. 1 is a top perspective view of one embodiment of a hand orthosis embodying various features of the present invention.

Referring initially to FIG. 1, one embodiment of the present invention includes a hand orthosis 10 having a palm area 12 in which a hand 14 is positioned for support of a patient's fingers 16 and right or left thumb 18 in a spaced apart configuration during a medical treatment procedure performed on the patient. When positioned in the palm area 12, the hand orthosis 10 supports the fingers 16 and thumb 18 of either the right or left hand. The hand orthosis 10 provides for separation of the fingers 16 and thumb 18 from contact with each other, or with the palm of the patient's hand 14 during a medical treatment procedure such as arthroscopy. The hand orthosis 10 may be utilized for any surgery on the patient that does not involve the hand in which the hand orthosis 10 is positioned. By maintaining the fingers 16 and thumb 18 from contacting each other, or from contacting the patient's palm, the likelihood of nerve compression, skin ulceration, and/or blood flow restrictions within the digits of the hand are minimized during lengthy medical treatment procedures performed on other portions of a patient such as a shoulder arthroscopy.

Figure 2:
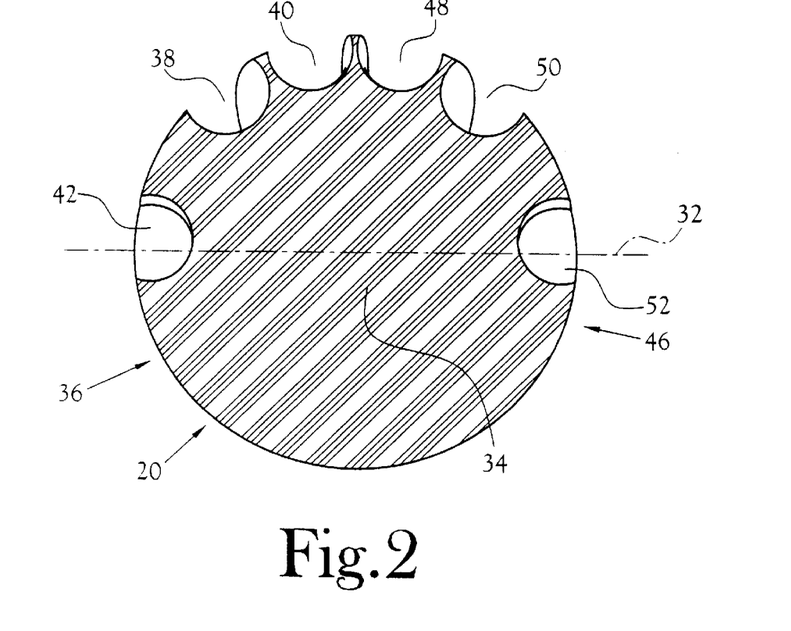
FIG. 2 is a cross section along 2—2 of FIG. 1, illustrating a spheroid body having a plurality of grooves positioned along an ellipsoidal surface of the present invention.

One embodiment of the hand orthosis 10 includes a spherical body 20 (see FIG. 2) having a preferred configuration of an oblate spheroid body 22 (see FIG. 1) composed of a porous material that is resiliently compressible. The spheroid body 20 includes an ellipsoidal outer surface 24 having a major axis 26 and a minor axis 32. The major axis 26 includes the length between a first end 28 and a second end 30 (see FIG. 1). A minor axis 32 includes the width of the spheroid body 22 (see FIG. 2). An interior 34 of the oblate spheroid body 22 may include a compressible material such as foam material, or a foam material encircling a solid core or a central void (not shown).

The ellipsoidal outer surface 24 includes a left hemisphere 36 having at least two elongated finger grooves 38, 40 thereon. The ellipsoidal outer surface 24 further includes a right hemisphere 46 having at least two elongated finger grooves 48, 50 thereon. The plurality of finger grooves are elongated to extend substantially parallel along the major axis 26 between the first end 28 and the second end 30 of the oblate spheroid body 22. An alternative embodiment for the plurality of finger grooves 38, 40, 48, 50, includes ends of each groove extended somewhat outwardly towards the second end 30 of the hand orthosis 10 to maintain separation of each finger from contact with an adjacent finger.

A first angled groove 42 extends along the left hemisphere 36, and a second angled groove 52 extends along the right hemisphere 46. Each angled groove 42, 52 is oriented to extend in an angled orientation across the respective left hemisphere 36 and right hemisphere 46 at an angle of between about twenty degrees to about forty-five degrees from an adjacent finger groove for accommodation of the angle of a relaxed thumb 18 in relation to an extended forefinger of either hand 14.

Each finger and thumb groove is shaped as an elongated indentation into the outer surface 24. Each groove includes a cross-section of a semi-circle (see FIG. 2), and includes a depth of between about one-half cm to about one cm. The length of the finger grooves varies significantly between the small, medium, and large sizes provided for the hand orthosis 10. A typical finger groove length includes a range of about two inches to about four inches in length for each finger groove 38, 40, 48, 50 (see FIG. 1). A typical thumb groove length includes a range of about two inches to about four inches in length for each thumb groove 42, 52 (see FIG. 1).

Figure 3:
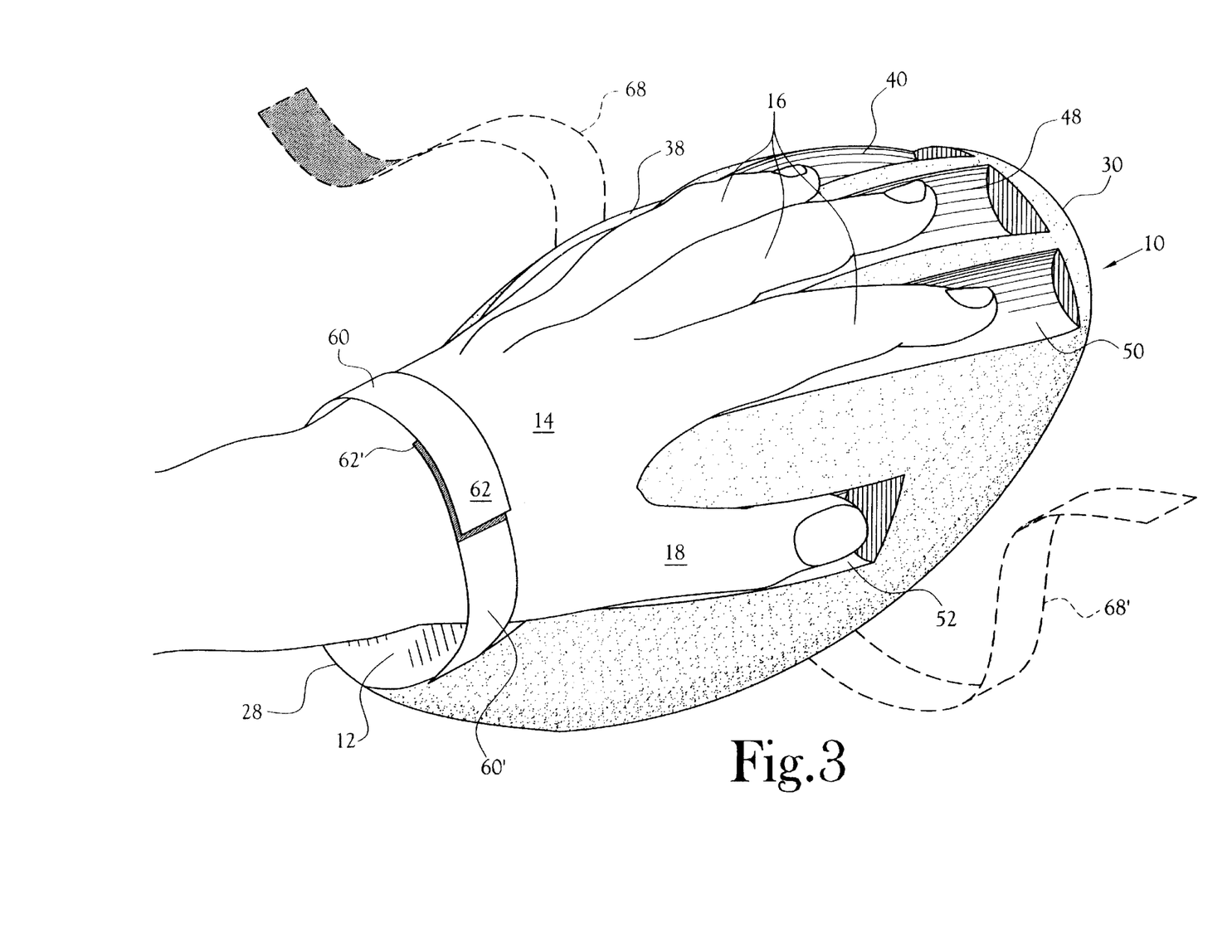
FIG. 3 is a side perspective view of FIG. 1, illustrating means for fastening the patient's hand on the oblate spheroid body of the hand orthosis.

A means for fastening of the hand orthosis 10 to the hand 14 includes two overlapping and connectable straps 60, 60' (see FIG. 3). Each strap includes a first end portion connected on the left hemisphere 36, and on the right hemisphere 46 proximate the first end 28 of the hand orthosis 10. Each strap 60, 60' includes an adequate length for extension outwards from the first end 28 a sufficient distance to allow each respective distal end 62, 62' of each strap to overlay each other. On each distal end 62, 62' is a connecting mechanism such as a plurality of hook fasteners 64 and loop type fasteners 66 positioned to face each other on the respective overlapping surfaces. Each hook and loop type fastener is positioned to encircle the hand or wrist of the patient and to releasably contact each other when the oblate spheroid body 22 is positioned against patient's hand 14.

An alternative embodiment for the means for fastening is two separate pairs of overlapping and connectable straps 60, 60' (see FIG. 3) and 68, 68' (in phantom in FIG. 3). The first pair of overlapping straps 60, 60' is connected proximate to the first end 28 of the hand orthosis 10. The second pair of overlapping straps 68, 68' is connected proximate to the mid-portion of the left hemisphere 36 and the right hemisphere 46 of the hand orthosis 10. Each overlapping strap includes an adequate length to extend outwards from the oblate spheroid body 22, to allow each respective distal end 62, 62' of each strap to overlay each other. On each distal end 62, 62' is a connecting mechanism such as a plurality of hook fasteners 64 and loop type fasteners 66 positioned to face each other on the respective overlapping surfaces of distal ends 62, 62'. Each overlapping strap 60, 60' and 68, 68' is positioned to encircle the hand or wrist of the patient when the hand orthosis 10 is placed against the patient's hand 14. The hook and loop type fasteners are releasably contacted against each other for maintaining the patient's fingers and thumb within the respective grooves on the oblate spheroid body 22. Those skilled in the art will recognize that alternative connecting mechanisms may be utilized such as snaps, buckles, and similar connectors for fastening the two distal ends of the overlapping straps together.

The hand orthosis 10 is reusable and includes a generally flexible outer surface 24 composed of a plastic material or similar material that is resistant to absorption of liquids and is resistant to repetitive cleaning with alcohol-based cleaner solutions. The hand orthosis 10 is provided in at least three sizes, such as small, medium, and large, to provide adequate fit of the hand orthosis 10 within a petite child patient's hand, a woman's hand, or a large adult patient's hand.

Those skilled in the art will recognize additional uses of the hand orthosis 10 including positioning of an oblate spheroid body 22 in each hand of an elderly patient, or within a hand of an arthritic patient for periodic exercising of one or both hands. In addition, an oblate spheroid body 22 may be positioned in each hand of a critically ill patient, for maintenance of the preferred spacing of the fingers from the thumb and from the palm of the hand, during long-term treatment of the conscious or unconscious patient.

Figure 4:
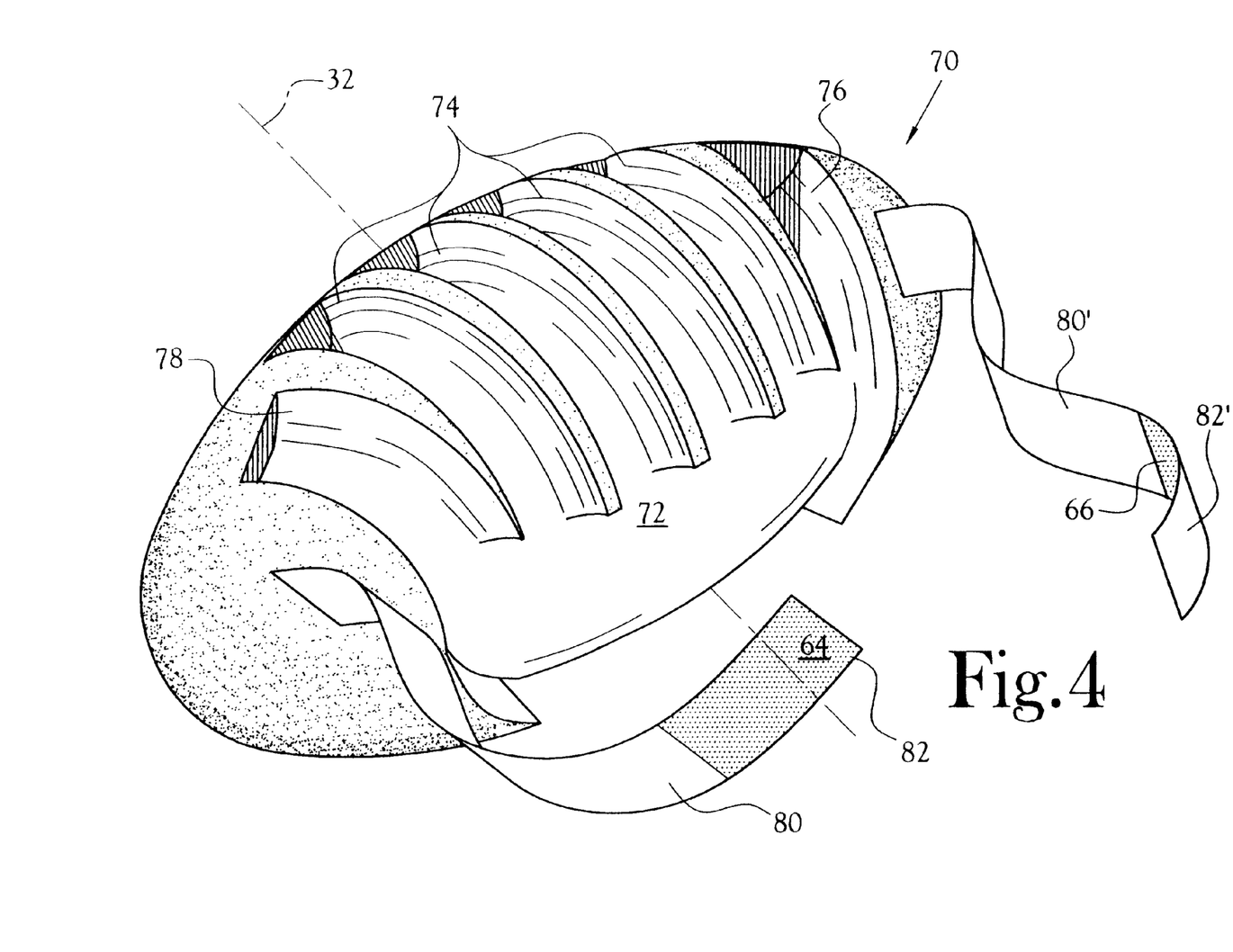
FIG. 4 is a side perspective view of an alternative embodiment of a hand orthosis having a plurality of grooves positioned across an ellipsoidal surface of the hand orthosis.

An alternative configuration of a hand orthosis 70 includes an orientation of at least four finger grooves 74 in a substantially parallel orientation with the minor axis 32 (see FIGS. 4). The hand orthosis 70 includes an ellipsoidal outer surface having a palm area 72 and at least four finger grooves 74 oriented across the right hemisphere 46 and the left hemisphere 36, with each finger groove being substantially parallel with the minor axis 32. The thumb grooves 76, 78 are spaced apart from, and positioned on opposed sides of the at least four finger grooves 74.

A means for fastening of the hand orthosis 70 to the patient's hand 14 includes two overlapping and connectable straps 80, 80' (see FIG. 4) attached proximate a first end and a second end of the hand orthosis 70. An alternative embodiment for the means for fastening includes two separate pairs of overlapping and connectable straps 60, 60' and 68, 68' (see FIG. 3). Each overlapping strap includes an adequate length to extend outwards from the connecting end to the egg-shaped body, to allow each respective distal end 82, 82' of each strap to overlap each other. On each distal end 82, 82' of each strap is a connecting mechanism such as a plurality of hook fasteners 64 and loop type fasteners 66 positioned respectively on each overlapping surface. The two overlapping and connectable straps 80, 80' are positioned to encircle the hand or wrist of a patient when hand orthosis 10 is placed against the patient's hand 14. A further alternative means for fastening may include elastic webbing material (not shown) that covers each respective finger groove 38, 40, 48, 50 or 74, and inserting the fingers of the hand under the webbing material. The elastic webbing material may further include material that covers each respective thumb groove 42, 52. Other materials known to those skilled in the art for fastening a hand to a hand-held object may be utilized.

Figure 5:
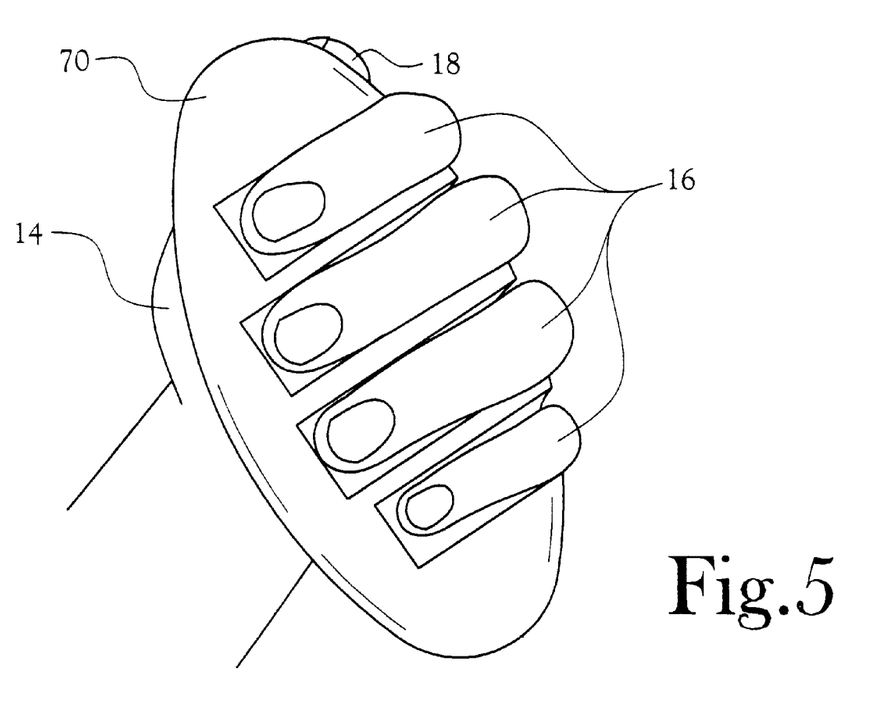
FIG. 5 is a top perspective view of FIG. 4, illustrating means for fastening the patient's hand on the alternative embodiment of the hand orthosis.
Figure 6:
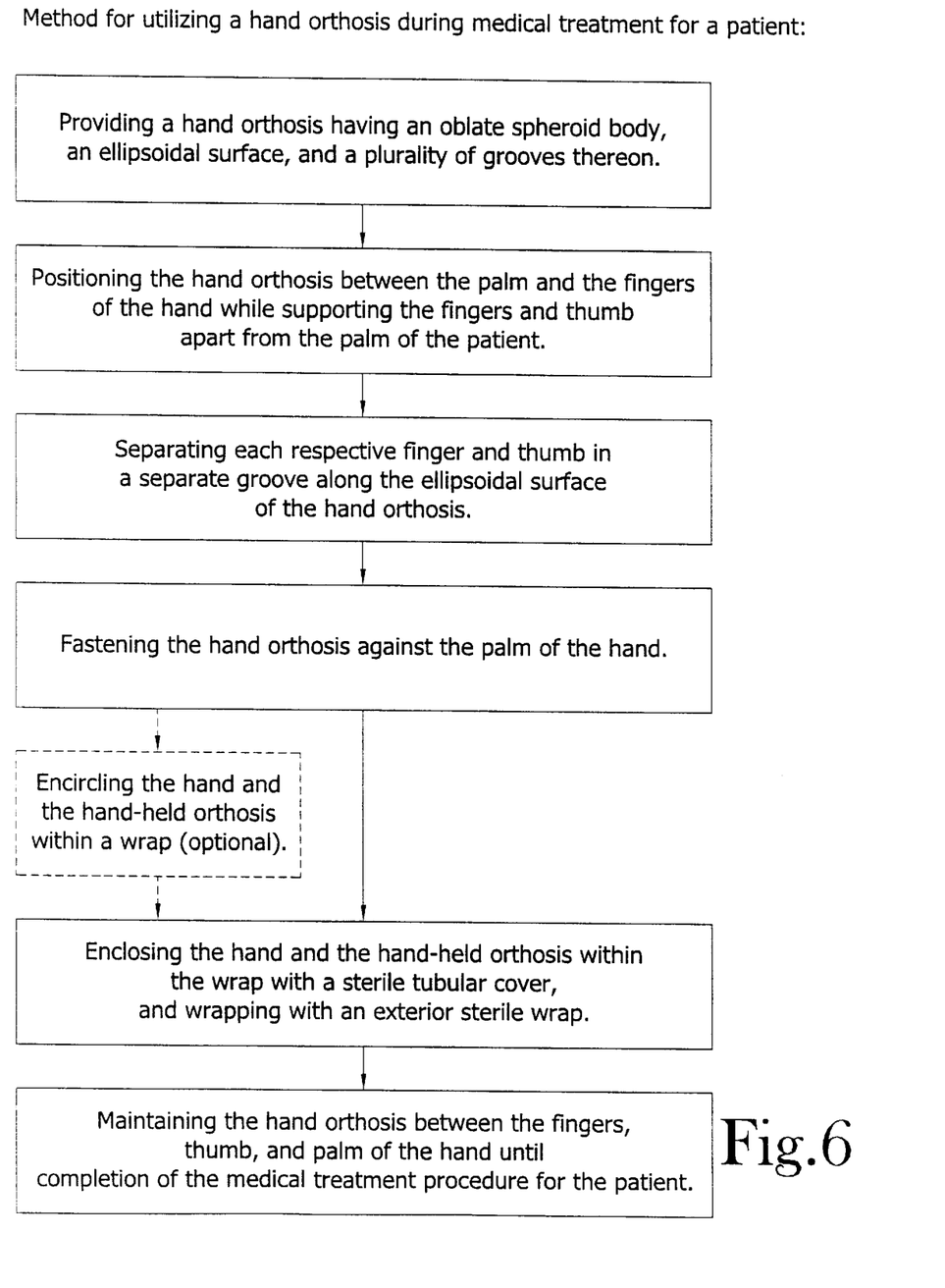
FIG. 6 is a schematic of the steps of the method for utilizing a hand orthosis having an oblate spheroid shape and a plurality of grooves thereon during a medical treatment procedure for an arm and shoulder of a patient.

A method of utilizing the hand orthosis 10, 70 during a medical treatment procedure for a patient includes a plurality of steps (see FIG. 6), including the step of providing a hand orthosis 10 having an oblate spheroid body 22, an ellipsoidal surface 24, and a plurality of grooves 38, 40, 42, 48, 50, 52 (see FIGS. 1, 3). An alternate step of providing may include providing an alternative hand orthosis 70 having an egg-shaped body having a plurality of grooves 74 and left thumb groove 76 and right thumb groove 78 (see FIGS. 4 and 5).

Figures 7, 8:
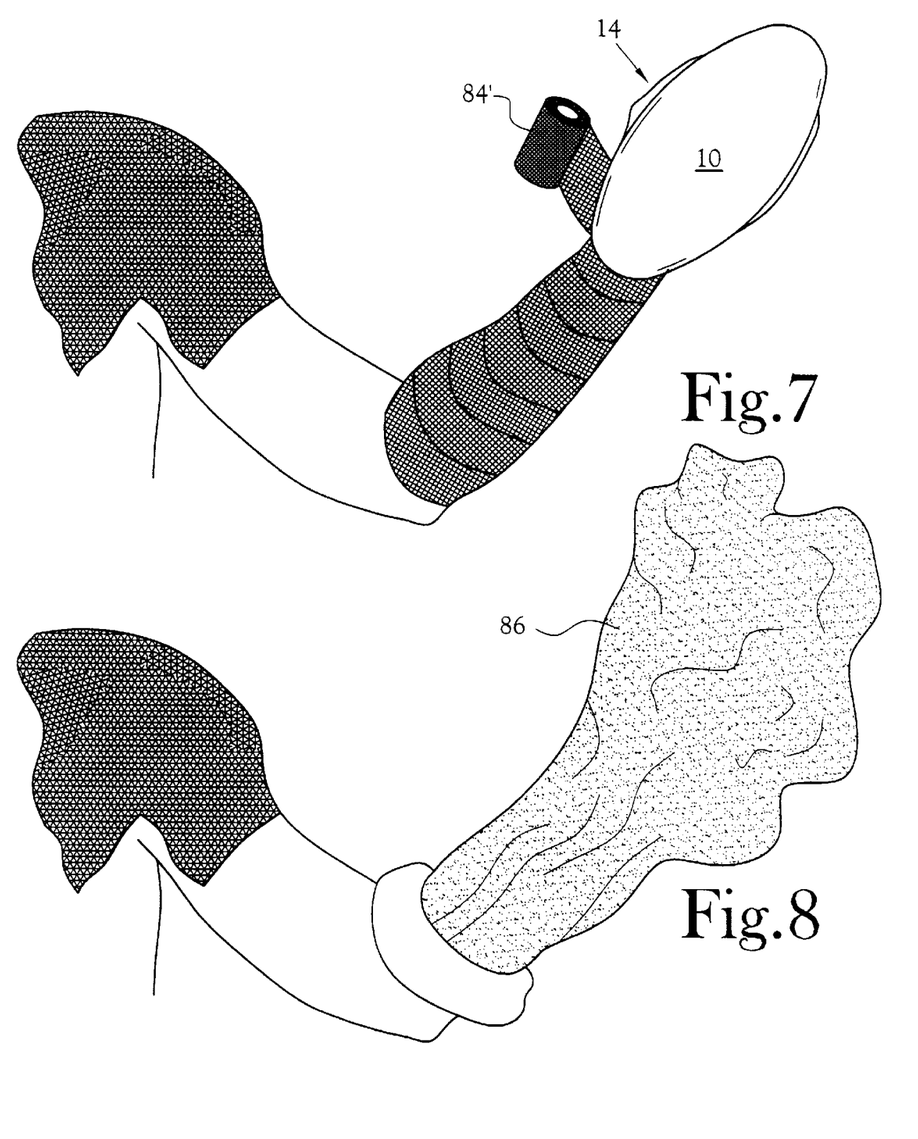
FIG. 7 is a perspective view of a patient holding the hand orthosis during an alternative step of preparation of the arm for a medical treatment procedure.
FIG. 8 is a perspective view of a patient having a hand and a forearm wrapped to enclose the hand orthosis within the hand.

The step of providing a hand orthosis 10, 70 is followed with a step of positioning the patient's hand against the palm area 12, 72 while supporting the fingers 16 and thumb 18 apart from each other in each respective groove of the plurality of grooves (see FIG. 7).

The step of positioning is followed with a step of supporting each respective finger 16 and thumb 18 in each one of the separated grooves along the ellipsoidal surface 24 of the hand orthosis 10, 70 (see FIG. 7).

The steps of positioning and supporting are followed by a step of fastening the hand orthosis 10, 70 with means for fastening against the palm of the hand. The means for fastening includes positioning at least two straps attached to opposed sides or ends of the hand orthosis 10, 70, with the at least two straps fastened together at distal ends of the straps with a fastening mechanism known to those skilled in the art, such as a hook and loop fastening system. An alternative means for fastening may include elastic webbing material (not shown) that covers each respective finger grooves 38, 40, 48, 50 or 74, and inserting the fingers of the hand under the webbing material.

The step of fastening may be followed by an alternative step of encircling the hand 14 and the hand orthosis 10, 70 within a wrap 84' (see FIG. 7) while maintaining the patient's hand 14 against the palm area 12, 72 of the hand orthosis 10, 70. The wrap 84' may include a sterile elastic band wrapped around the exterior of the hand 14, while the curved fingers 16 and thumb 18 are positioned within each groove of the hand orthosis 10, 70.

Regardless of whether the step of encircling is utilized, an enclosing step follows the fastening step and/or the encircling step for enclosing the hand 14 and the hand orthosis 10, 70 within a sterile cover 86 (see FIG. 8), while maintaining the separation of each finger and thumb of the hand 14 until completion of the medical treatment procedure for the patient. The sterile cover 86 includes a covering for a forearm that is known to those skilled in the art, such as a tubular stockinette having a sterile exterior surface. The enclosing step forms a sterile boundary between the wrapped hand 14 holding the hand orthosis 10, 70, and the patient's body.

Figure 9:
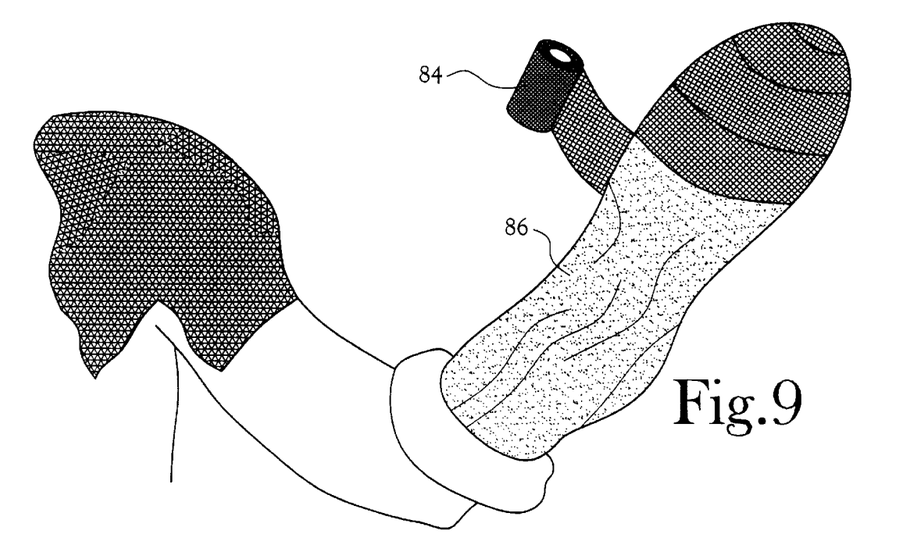
FIG. 9 is a perspective view of a patient having the enclosed hand holding the hand orthosis and a forearm wrapped in preparation for a medical treatment procedure.
Figure 10:
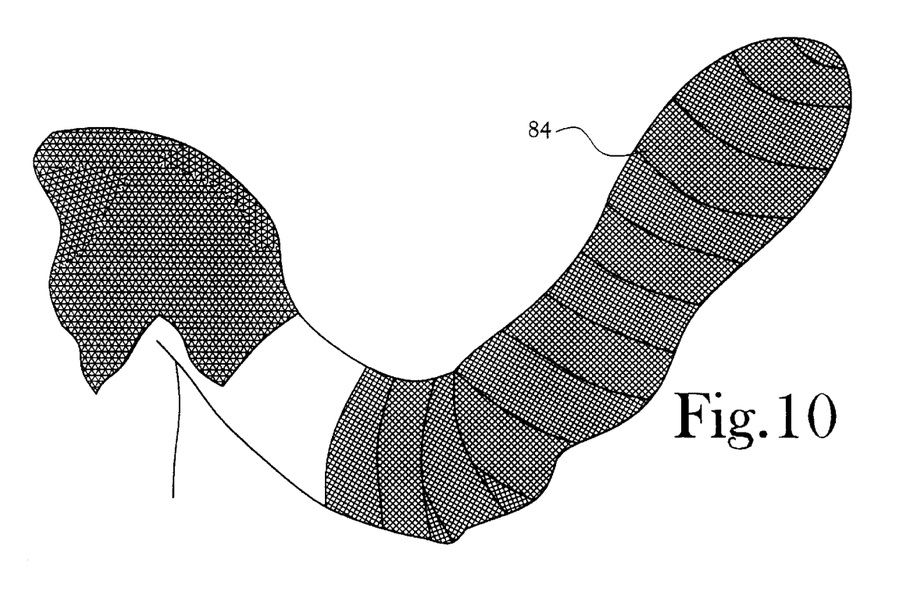
FIG. 10 is a perspective view of a patient having a hand holding the hand orthosis and a forearm prepared for a medical treatment procedure.

The step of enclosing the hand within a sterile cover 86 is followed by a step of wrapping the sterile cover 86 with additional elastic tape 84 around the exterior of the sterile cover 86 (see FIGS. 9 and 10). The method maintains the hand orthosis 10, 70 between the fingers, thumb, and palm of the hand until completion of the medical treatment procedures for the patient.

While a preferred embodiment for the foregoing device and method of utilizing the device is shown and described, it will be recognized that alternative embodiments of the disclosed invention may be employed without departing from the spirit and the scope of the invention as set forth in the appended claims.

Having thus described the aforementioned invention I claim:

1. A hand orthosis for support of a patient's fingers in a spaced apart configuration to separate the fingers from contact with each other and from contact with a palm of the patient's hand during an extended period of time, comprising:

a body member having an ellipsoidal surface and an oblate spheroid shape having a major axis and a minor axis;

a plurality of grooves indented in said ellipsoidal surface in spaced a art configuration and positioned in substantially parallel relation to each other along said ellipsoidal surface for placement of each one of the patient's fingers within each respective groove of said plurality of grooves;

a first and a second thumb groove positioned on opposed sides of said plurality of grooves and being angularly spaced apart from said plurality of grooves, said first and said second thumb groove being extended along said ellipsoidal surface for accommodation of a thumb of the patient's hand in either said first or said second thumb groove;

wherein said plurality of grooves maintain the fingers and thumb of the hand in spaced apart and curved configuration apart from the palm of the patient's hand when said body member is positioned against the palm of the patient's hand during an extended time period; and a retainer means attached to said body member, said retainer means releasably encircling the patient's hand to maintain said ellipsoidal surface against the palm of the hand, said retainer means renders the palm of the hand substantially immovable relative to the fingers and thumb of the hand, said body member further including a palm area for the palm of the hand to be maintained against said palm area, the palm of the hand rendered substantially immovable relative to said palm area by said retainer means when each one of the patient's fingers are separately placed within each respective groove of said plurality of grooves and the thumb of the patient's hand is placed in either the first or the second thumb groove.

2. The hand orthosis of claim 1, wherein said plurality of grooves includes at least four finger grooves being aligned and extended substantially parallel with the major axis of said body member.

3. The hand orthosis of claim 1, wherein said plurality of grooves includes at least four finger grooves being aligned and extended substantially parallel with the minor axis of said body member.

4. The hand orthosis of claim 1, wherein said first and said second thumb groove being extended in angularly spaced apart orientation on opposed sides of said plurality of grooves, said first thumb groove receives the thumb of a first hand of the patient, and said second thumb groove receives the thumb of a second hand of the patient when said body member having an oblate spheroid shape is positioned against the palm of the patient's first or second hand.

5. The hand orthosis of claim 2, wherein said retainer means includes a first strap extended from a first end of said body member, and a second strap extended from an opposed side of said first end of said body member, said first strap and said second strap having respective first and second distal ends extendable to overlay each other, said first distal end of said first strap and said second distal end of said second strap having a hook and a loop type fastener positioned respectively on each distal end for releasably fastening of said first and said second distal end to each other when said oblate spheroid shaped body member is positioned against the palm of the patient's hand.

6. The hand orthosis of claim 3, wherein said retainer means includes a first strap extended from a first end of said body member, and a second strip extended from a second end of said body member, said first strap and said second strap having respective first and second distal ends extendable to overlay each other, said first distal end of said first strap and said second distal end of said second strap having a hook and a loop type fastener positioned respectively on each distal end for releasably fastening of said first and said second distal end to each other when said oblate spheroid shaped body member is positioned against the palm of the patient's hand.

7. The hand orthosis of claim 5, wherein said retainer means includes said first and said second strap extended from said first end of said body member, and a second pair of straps extended from said body member proximate a middle portion of said body member, each pair of straps having respective first and second distal ends extendable to overlay each other, said first distal end of each pair of straps and said second distal end of each pair of straps having a hook and a loop type fastener positioned respectively on each distal end for releasably fastening of each of said pair of first and said second distal end to each other when said body member is positioned against the palm of the patient's hand.

8. The hand orthosis of claim 1, wherein said body member having an oblate spheroid shape includes a porous material therein, said porous material is resiliently compressible by the patient's fingers and thumb when said retainer means maintains said body member within the palm of the hand during the extended period of time.

9. A hand orthosis for support and separation of a patient's fingers in a spaced apart configuration during an extended period of time, comprising:
 a body member having an oblate spheroid shape and an ellipsoidal surface, said body member having a first end and a second end;
 a plurality of grooves indented along said ellipsoidal surface in space apart configuration between said first end and said second end, said plurality of grooves positioned in substantially parallel relation to each other for each one of the patient's fingers to be positioned within each respective groove of said plurality of grooves;
 a first and a second thumb groove positioned on opposed sides of said plurality of grooves and being angularly spaced apart from said plurality of grooves, said first and said second thumb groove being extended along said ellipsoidal surface for accommodation of a thumb of the patient's hand in either said first or said second thumb groove; and
 means for fastening said body member within the palm of the hand, said means for fastening maintains the palm of the patient's hand against said ellipsoid surface, said body member further including a palm area for the palm to be maintained against with each one of the patient's fingers and the respective thumb positioned within each respective groove in spaced apart configuration, said means for fastening maintains said body member against the palm of the hand to maintain contact of the palm, fingers and the respective thumb against said ellipsoidal surface;
 wherein said plurality of grooves maintain the fingers and thumb of the hand in spaced apart and curved configuration when said body member is positioned against the palm of the patient's hand during an extended time period.

10. The hand orthosis of claim 9, wherein said plurality of grooves being aligned with a major axis extended between said first end and said second end of said body member, said plurality of grooves having at least four finger grooves being extended in substantially parallel alignment with said major axis of said body member.

11. The hand orthosis of claim 9, wherein said plurality of grooves being aligned with a minor axis of said body member, said plurality of groove having at least four finger grooves being extended in substantially parallel alignment with said minor axis of said body member.

12. The hand orthosis of claim 10, wherein said means for fastening includes a first strap extended from said first end of said body member, and a second strap extended from an opposed side of said ellipsoidal surface from said first end, said first strap and said second strap having respective first and second distal ends extendable of overlay each other, said first distal end of said first strap and said second distal end of said second strap having a hook and a loop type fastener positioned respectively on each distal end for releasably fastening of said first and said second distal end to each other when said body member having said oblate spheroid shape is positioned against the palm of the hand.

13. The hand orthosis of claim 11, wherein said means for fastening includes a first strap extended from said first end of said body member, and a second strap extended from said second end of said body member, said first strap and said second strap having respective first and second distal ends extendable to overlay each other, said first distal end of said first strap and said second distal end of said second strap having a hook and a loop type fastener positioned respectively on each distal end for releasably fastening of said first and said second distal end to each other when said oblate spheroid shape of said body member is positioned against the palm of the patient's hand.

14. A method of utilizing a hand orthosis for separating a patient's fingers and thumb from contacting each other during a medical treatment procedure for the patient's body, comprising the steps of:
 (a) providing a hand orthosis including an ellipsoidal surface having plurality of grooves thereon;
 (b) positioning said hand orthosis within the palm and the fingers of the hand with each finger and thumb of the patient in a respective groove of said plurality of grooves on said hand orthosis;
 (c) fastening said hand orthosis against the palm of the patient's hand; and
 (d) enclosing the hand and said hand orthosis against the palm of the patient's hand with a sterile cover, whereby said enclosing step defines a sterile boundary between the patient's hand, said hand orthosis and an operative site of the medical treatment procedure for the patient's body.

15. The method of claim 14, wherein said step of providing including providing said hand orthosis having an oblate spheroid body member supporting each respective finger and thumb in a separate groove of said plurality of grooves, said step of positioning including supporting each respective finger apart from each other finger and thumb of the hand during said steps of positioning, fastening and enclosing.

16. The method of claim 15, wherein said step of positioning further including positioning each one of the fingers of the hand within each respective groove of said plurality of grooves, said step of positioning maintaining each finger and thumb apart from the palm of the hand during said steps of positioning, fastening and enclosing.

17. The method of claim 16, wherein said step of positioning including positioning the thumb of the patient's hand within one of two thumb groove of said plurality of grooves, said thumb grooves angled apart from said plurality of grooves having fingers positioned therein, said step of positioning supporting the thumb apart from each other finger and apart from the palm of the hand during said steps of positioning, fastening and enclosing.

18. The method of claim 17, wherein said step of fastening said hand orthosis against the palm of the hand including extending at least two straps in overlapping orientation from said hand orthosis, said step of fastening further including said at least two straps having respective means for releasably fastening each of said at least two straps against each other for encircling the hand or wrist of the patient, thereby maintaining the palm of the hand against said hand orthosis during said fastening and enclosing steps when said hand orthosis is positioned against the palm of the patient's hand.

19. The method of claim 18, wherein said method further includes said step of fastening is followed by a step of encircling the hand and said hand orthosis within a sterile wrap, said steps of fastening and encircling maintaining each respective finger and thumb in a separate groove of said plurality of grooves, said step of encircling maintains a sterile boundary between the patient's hand and said hand orthosis and the operative site during a medical treatment procedure.

20. The method of claim 19, wherein said method further includes said step of enclosing is followed by a step of wrapping the enclosed hand and said hand orthosis against the palm of the hand with an additional sterile wrap, said wrapping step maintaining the sterile boundary between the enclosed hand holding said hand orthosis and the operative site during the medical treatment procedure for the patient.

\* \* \* \* \*